United States Patent
Kust et al.

(10) Patent No.: US 6,712,794 B2
(45) Date of Patent: Mar. 30, 2004

(54) APPARATUS FOR DELIVERING A VISCOUS LIQUID TO A SURGICAL SITE

(75) Inventors: Richard Kust, Aliso Viejo, CA (US); Gary Werschmidt, Yorba Linda, CA (US); William Porter, Carlsbad, CA (US); Robert Keahy, San Antonio, CA (US); Gary Aurin, Foothill Ranch, CA (US); Roger Massengale, Mission Viejo, CA (US)

(73) Assignee: Spinal Specialties, Inc., San Antonio, TX (US)

(*) Notice: Subject to any disclaimer, the term of this patent is extended or adjusted under 35 U.S.C. 154(b) by 68 days.

(21) Appl. No.: 09/934,435

(22) Filed: Aug. 21, 2001

(65) Prior Publication Data

US 2003/0040718 A1 Feb. 27, 2003

(51) Int. Cl.⁷ .................. A61M 50/00; A61M 5/315
(52) U.S. Cl. .................. 604/224; 604/211; 604/235
(58) Field of Search .................. 604/181, 187, 604/218, 228, 240, 241, 15, 18, 59, 186, 188, 207, 208, 209, 210, 211, 220, 221, 224, 225, 235

(56) References Cited

U.S. PATENT DOCUMENTS

| | | |
|---|---|---|
| 2,472,116 A | 6/1949 | Maynes |
| 2,565,081 A | 8/1951 | Maynes |
| 2,591,457 A | 4/1952 | Maynes |
| 3,880,163 A | 4/1975 | Ritterskamp |
| 3,882,863 A | 5/1975 | Sarnoff et al. |
| 4,312,343 A | 1/1982 | LeVeen et al. |
| 4,316,463 A | 2/1982 | Schmitz et al. |
| 4,381,006 A | 4/1983 | Genese |
| 4,530,695 A | 7/1985 | Phillips et al. |
| 4,597,754 A | 7/1986 | Thill et al. |
| 4,623,330 A | 11/1986 | Laby et al. |
| 4,755,172 A | 7/1988 | Baldwin |
| 4,966,585 A | 10/1990 | Gangemi |
| 4,997,420 A | 3/1991 | LeFevre |
| 5,078,679 A | 1/1992 | Reese |
| 5,100,389 A | 3/1992 | Vaillancourt |
| 5,178,609 A | 1/1993 | Ishikawa |
| 5,300,030 A | 4/1994 | Crossman et al. |
| 5,318,539 A | 6/1994 | O'Neill |

(List continued on next page.)

FOREIGN PATENT DOCUMENTS

| | | |
|---|---|---|
| DE | 4222470 | 7/1992 |
| EP | 0584569 | 3/1994 |
| GB | 624958 | 6/1949 |
| GB | 2 266 463 A | 11/1993 |
| GB | WO 99/65597 | 12/1999 |
| WO | 94/07553 | 4/1994 |
| WO | 95/00193 | 1/1995 |

Primary Examiner—Brian L. Casler
Assistant Examiner—Mark K. Han
(74) Attorney, Agent, or Firm—Klein, O'Neil & Singh, LLP

(57) ABSTRACT

Apparatus for delivering a viscous liquid to a surgical site employs a conventional syringe having a barrel and a plunger movable axially within the barrel from a withdrawn position to an inserted position. The apparatus includes an internally-threaded sleeve and a substantially cylindrical actuation element. The sleeve is configured to receive the plunger in its withdrawn position, and has an open proximal end and a distal end slot configured for receiving the syringe barrel therethrough. The actuation element has an externally-threaded distal portion dimensioned to screw into the proximal end of the sleeve, and a plunger seat, at the distal end of the actuation element, that bears against the plunger and that pushes the plunger axially toward its inserted position in the barrel as the actuation element is threaded into the sleeve.

19 Claims, 3 Drawing Sheets

U.S. PATENT DOCUMENTS

| | | | |
|---|---|---|---|
| 5,320,609 A | * | 6/1994 | Haber et al. ................. 604/135 |
| 5,330,430 A | | 7/1994 | Sullivan |
| 5,383,858 A | | 1/1995 | Reilly et al. |
| 5,425,715 A | | 6/1995 | Dalling et al. |
| 5,454,793 A | | 10/1995 | Levander et al. |
| 5,456,388 A | | 10/1995 | Honstein et al. |
| 5,599,309 A | | 2/1997 | Marshall et al. |
| 5,599,315 A | * | 2/1997 | McPhee ..................... 604/135 |
| 5,800,405 A | * | 9/1998 | McPhee ..................... 604/135 |
| 6,019,747 A | | 2/2000 | McPhee |
| 6,431,743 B1 | * | 8/2002 | Mizutani et al. ............ 366/189 |

\* cited by examiner

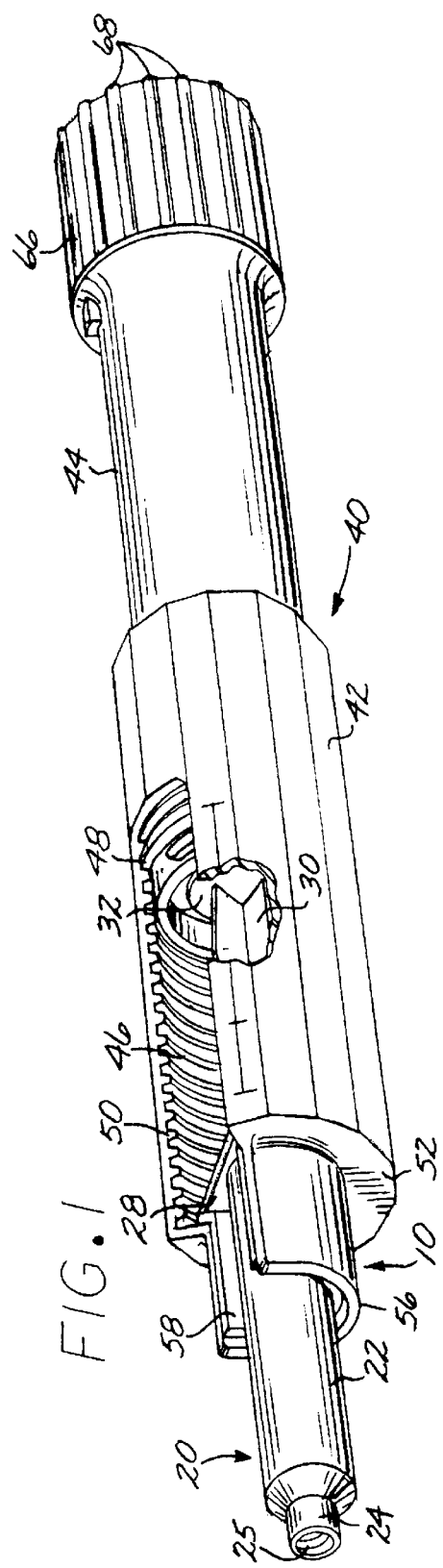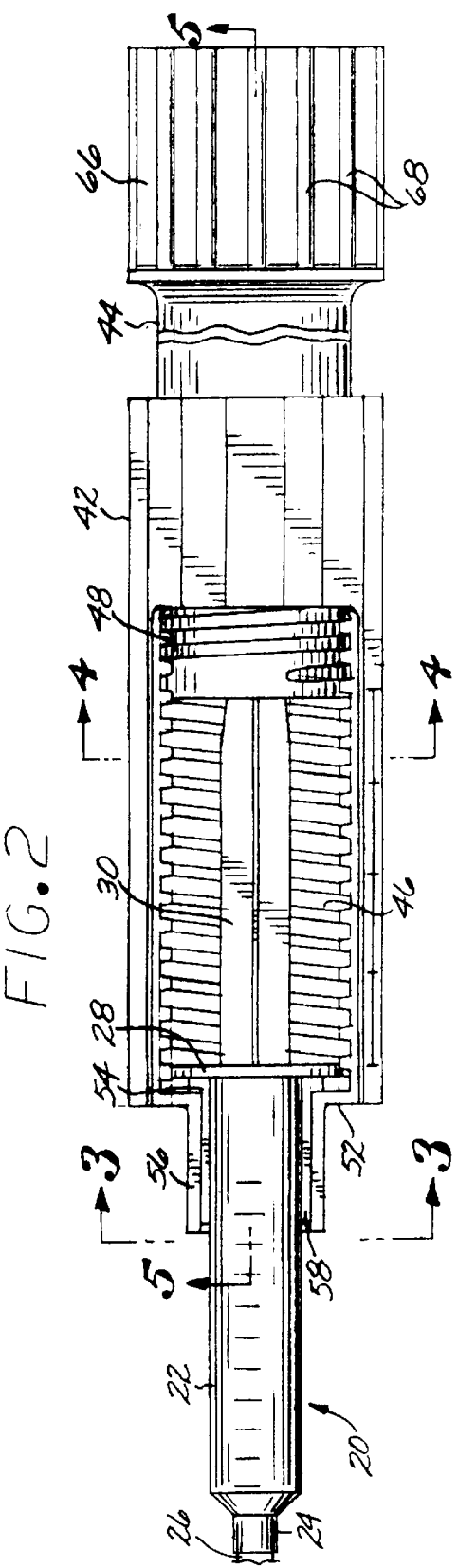

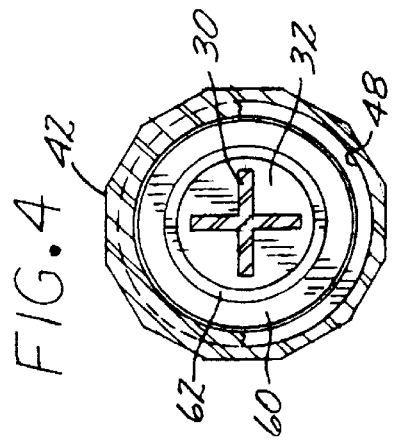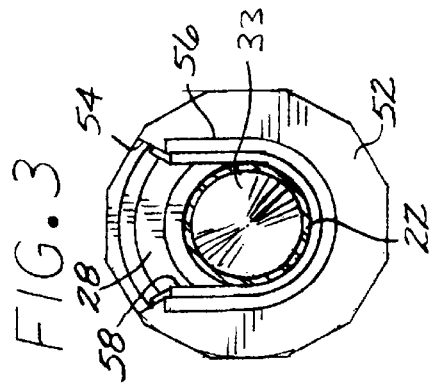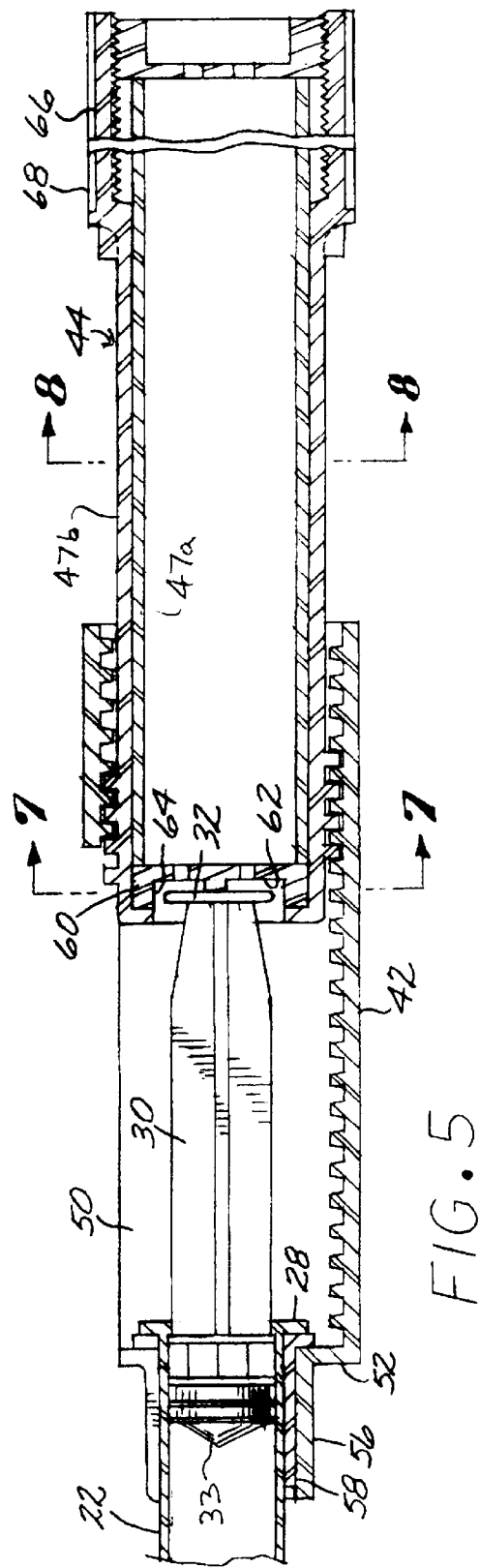

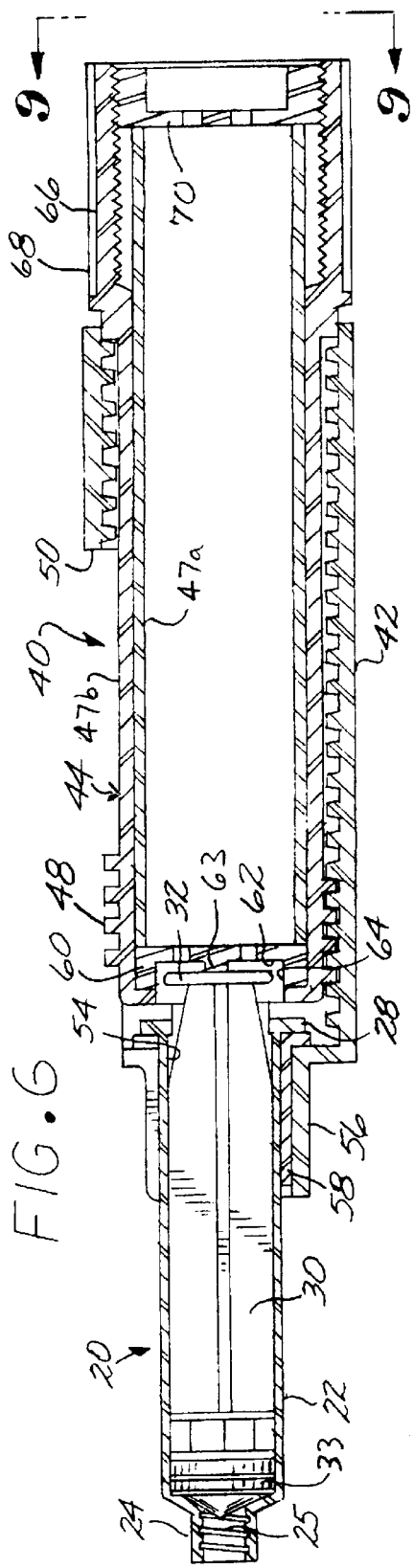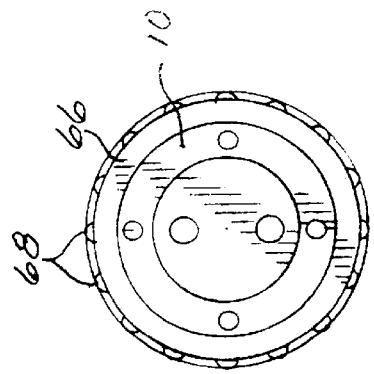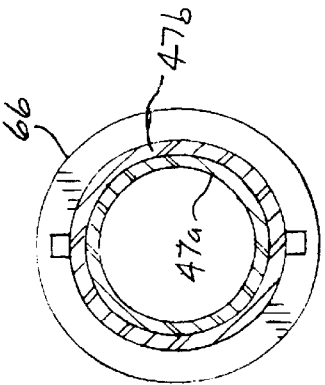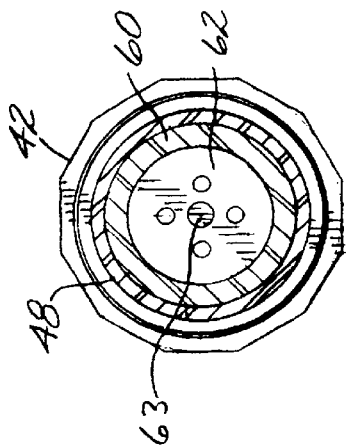

US 6,712,794 B2

APPARATUS FOR DELIVERING A VISCOUS LIQUID TO A SURGICAL SITE

CROSS REFERENCE TO RELATED APPLICATIONS

Not Applicable

FEDERALLY SPONSORED RESEARCH OR DEVELOPMENT

Not Applicable

BACKGROUND OF THE INVENTION

The present invention relates to an apparatus for delivering a viscous liquid material to a surgical site within the body of a human or an animal. More specifically, it relates to an apparatus for controllably delivering bone cement to a site within a bone that has been surgically prepared to receive the cement.

Many procedures in orthopedic surgery require a predetermined quantity of bone cement to be delivered to a site within a bone that has been surgically prepared to receive the cement. For example, surgery to correct certain spinal injuries or deformities requires a hole to be drilled or bored in a vertebra, and then the hole is filled with bone cement. This is accomplished by filling a syringe with bone cement, and then delivering the cement to the site via a cannula attached to the syringe by a length of flexible tubing.

Because the cement is quite thick and viscous, delivering the cement from the syringe requires a great deal of effort applied to the syringe plunger. Thus, both strength and dexterity are required on the part of the surgeon performing the procedure.

It would thus be an improvement over the current state of the art to provide a mechanism that would facilitate the delivery of bone cement and like materials by making it easier to express the material from the syringe.

SUMMARY OF THE INVENTION

Broadly, in one aspect, the present invention is an apparatus for delivering a viscous liquid to a surgical site, comprising a syringe having a barrel and a plunger movable axially within the barrel from a withdrawn position to an inserted position, and a syringe actuation device, wherein the syringe actuation device comprises (1) a hollow, internally-threaded sleeve configured to receive the plunger in its withdrawn position, the sleeve having an open proximal end and a distal end opening configured for securing the syringe barrel; and (2) a substantially cylindrical actuation element having (a) an externally-threaded distal portion dimensioned to screw into the proximal end of the sleeve, and (b) a plunger seat, at the distal end of the actuation element, that bears against the plunger and that pushes the plunger axially toward its inserted position in the barrel as the actuation element is threaded into the sleeve.

In another aspect, the invention is a syringe actuation device for receiving and holding a pre-filled conventional syringe having a barrel containing a measure of liquid and a plunger that is axially movable into the barrel for expressing the contents therefrom, the device comprising a sleeve for securing the pre-filled syringe with the plunger in a withdrawn position and an actuation element that screws into the sleeve so as to push the plunger into the barrel to express the liquid from the syringe.

In a specific preferred embodiment, the actuation device comprises an internally-threaded hollow sleeve with an open proximal end, and a substantially cylindrical actuation element with an externally-threaded distal portion that threads into the open proximal end of the sleeve. The actuation element includes a transverse (i.e., perpendicular to the actuation element axis) plunger seat at its distal end. The sleeve has a longitudinal opening parallel to its axis for receiving the extended plunger of a pre-filled syringe, and a distal end wall portion with an opening or slot through which the barrel of the syringe extends. Also, in the specific preferred embodiment, the proximal portion of the actuation element may be configured as an enlarged-diameter gripping element that is configured to facilitate actuation by increasing the mechanical advantage when the actuation element is screwed into the sleeve.

In use, the actuation element is backed out of the sleeve a sufficient distance in the proximal direction to allow a pre-filled syringe to be installed in the sleeve through the longitudinal opening. The barrel of the syringe being pre-filled with a measured volume of liquid, the plunger of the syringe is in its extended or withdrawn position. The outlet tip of the syringe is connected to one end of a fluid conduit, such as a length of flexible tubing, the other end of which may be coupled to an injection needle or a cannula. As the actuation element is threaded into the sleeve, the plunger seat bears against the plunger to push the plunger distally into the barrel until it reaches its fully inserted position, corresponding to the delivery of the measured volume of liquid from the barrel.

As will be appreciated that the threaded coupling between the actuation element and the sleeve allows the actuation element to be turned as a screw within the sleeve and to advance against the plunger with the mechanical advantage provided by a screw mechanism. This screwing action, in turn, allows the user more easily to apply sufficient force to the plunger to express a highly viscous liquid (e.g., bone cement) from the barrel. Furthermore, a greater degree of control can be used in actuating the plunger. For example, stopping the plunger at precise positions within the barrel, so as to express the contents of the barrel in desired increments, is greatly facilitated. These and other advantages of the invention will be more fully understood from the detailed description that follows.

BRIEF DESCRIPTION OF THE DRAWINGS

FIG. 1 is a perspective view of an apparatus for delivering a viscous fluid to a surgical site, in accordance with a preferred embodiment of the present invention, the apparatus comprising a syringe and a syringe actuation device;

FIG. 2 is a side elevational view, partially in section, of the apparatus of FIG. 1, showing the syringe and the actuation element of the syringe actuation device in their respective positions prior to actuation of the syringe and resultant delivery of its contents;

FIG. 3 is a transverse cross-sectional view taken along line 3—3 of FIG. 2;

FIG. 4 is a transverse cross-sectional view taken along line 4—4 of FIG. 2;

FIG. 5 is a longitudinal cross-sectional view taken along line 5—5 of FIG. 2;

FIG. 6 is a longitudinal cross-sectional view, similar to that of FIG. 5, but showing the syringe and the actuation element of the syringe actuation device in their respective positions after actuation of the syringe and the delivery of its contents;

FIG. 7 is a transverse cross-sectional view taken along line 7—7 of FIG. 5;

FIG. 8 is a transverse cross-sectional view taken along line 8—8 of FIG. 5; and

FIG. 9 is an end elevational view of the proximal end of the syringe actuation device, taken along line 9—9 of FIG. 6.

DETAILED DESCRIPTION OF THE INVENTION

Referring now to the drawings, an apparatus 10 for delivering a viscous liquid to a surgical site is shown, in accordance with a preferred embodiment of the invention. The apparatus 10 comprises a standard, conventional syringe 20 and a novel syringe actuation device 40. The syringe 20 comprises a barrel 22 that may be filled with a predetermined volume (typically, for example, 10 cc or 20 cc) of a liquid. In the present invention, the liquid is likely to be a highly viscous liquid, and, in particular, bone cement, but the invention is not limited to any specific type or viscosity of liquid.

The distal end of the barrel 22 tapers down to a distal outlet portion 24, which may be internally threaded (at 25) for coupling to a convention Luer fitting (not shown) at one end of a length of flexible tubing 26 (FIG. 2). The other end of the tubing 26 is typically coupled to needle or cannula (not shown) for introducing the liquid expressed from the syringe 20 to a surgical site (such as a bone, in the case of bone cement) within a patient's body. The proximal end of the barrel 22 is open and is surrounded by a peripheral flange 28.

The syringe 20 has a plunger 30 that is installed for axial movement within the barrel 22 between a withdrawn position (FIGS. 1, 2, and 5) and an inserted position (FIG. 6). The proximal end of the plunger 30 is advantageously configured as a flattened thumb rest 32, while the distal end of the plunger 30 is attached to a piston 33 sized for a sliding frictional engagement against the interior wall surface of the barrel 22.

The syringe actuation device 40 comprises a substantially cylindrical hollow sleeve 42 and a substantially cylindrical plunger actuation element 44 that is dimensioned to fit within the sleeve 42. The sleeve 42 has an open proximal end and internal threads 46, while the actuation element 44 comprises a substantially tubular inner member 47a coaxially disposed within a substantially cylindrical outer member 47b. The outer member 47b has a distal portion 48 that is externally threaded into the open proximal end of the sleeve 42.

The sleeve 42 has a longitudinal opening 50 parallel to its axis for receiving the extended plunger 30 of a pre-filled syringe 20 (as will be described below), and a distal end wall 52 with a distal slot 54 that is contiguous with the longitudinal opening 50, and that is dimensioned to receive the syringe barrel 22. The longitudinal opening 50 extends proximally from the distal end slot 54 at least half the length, and preferably about two-thirds to about three-quarters the length of the sleeve 42. Extending distally from the distal end wall 52 is a trough-like barrel securing member 56 that communicates with the distal end slot 54. The barrel securing member 56 is configured to hold the syringe barrel 22 with a friction fit, and thus has an inside diameter that is approximately the same as the outside diameter of the syringe barrel 22. A removable insert 58 may provided in the barrel securing member 56 to reduce the inside diameter of the barrel securing member 56 to accommodate a smaller syringe barrel 22. Thus, for example, the barrel securing member 56 without the insert 58 may be dimensioned to hold a 20 cc syringe, while the insert 58 may be installed if a 10 cc syringe is to be used.

Attached to the distal end of the inner member 47a of the actuation element 44 is a distal end cap that comprises a distally-extending peripheral rim 60 surrounding a substantially circular plunger seat 62. The rim 60 and the plunger seat 62 define a receptacle or recess 64 that is dimensioned to receive the thumb rest 32 at the proximal end of the syringe plunger 30. The plunger seat 62 may optionally be formed with one or more distally-extending protrusions 63 against which the thumb rest 32 seats.

The outer member 47b of the actuation element 44 has a proximal portion 66 that is advantageously of an enlarged diameter to provide a convenient hand grip. To this end, it may also be formed with longitudinal ridges 68 to provide a non-slip gripping surface. The proximal portion 66 may be internally threaded for the attachment of an externally-threaded proximal end cap 70.

In use, a syringe 20, pre-filled with a measured volume of a liquid (such as bone cement) contained in the barrel 22, is installed within the sleeve 42 through the longitudinal opening 50. The syringe barrel 22 being filled, the plunger 30 is in its withdrawn (proximal) position, extending proximally from the proximal end of the barrel 22. The barrel 22 of the syringe 20 extends through the distal end slot 54 of the sleeve 42, and it is snapped into place in the barrel securing member 56, which may be fitted with the insert 58 (as shown) or not, depending on the size (outside diameter) of the barrel. The barrel flange 28 is seated against the interior surface of the distal end wall 52 of the sleeve 42. The actuation element 44 may, at this point, be inserted into the proximal end of the sleeve 42 and threaded distally into the sleeve until the thumb rest 32 of the plunger 30 is received within the receptacle 64 in the distal end cap of the actuation element 44 and is seated against the plunger seat 62. Thus, as shown in FIGS. 1, 2, and 5, the apparatus 10 is ready for use to express the liquid contents of the barrel 22 out of the outlet tip 24 of the syringe 20, and to the surgical site through the conduit 26 and a needle or cannula (not shown) that is installed in the site.

To express the contents of the barrel, the actuation element 44 is threaded further distally within the sleeve 42, thereby pushing the plunger 30 distally, toward its inserted position within the barrel 22, through the engagement between the plunger seat 62 and the thumb rest 32. As shown in FIG. 6, this process may be continued until the plunger 30 is in its fully inserted (distal) position, at which point the entire volume of liquid contained within the barrel 22 has been emptied therefrom. It will be appreciated that this process can be interrupted at any desired position(s) of the plunger to express a part of the contents, or to express the contents in desired increments.

The screw mechanism action of the actuation element 44 within the sleeve 42 provides a marked mechanical advantage that facilitates the dispensing of highly viscous liquids, such as bone cement, from the syringe 20. Furthermore, the partial or incremental dispensing of the syringe contents can be more easily controlled, by means of the screw mechanism, as compared with manually actuating the plunger by pressure applied directly by the user's thumb. Contributing to the control is the characteristic that nearly the entire length of the barrel 22 is visible, both the proximal portion carried within the barrel securing member 56, and the distal portion that extends distally from the barrel securing member. In addition, syringe actuation device 30 can easily be re-used. The empty syringe can easily be removed and replaced with a new syringe.

While a preferred embodiment of the invention has been described herein, it will be appreciated that a number of modifications and variations will suggest themselves to those skilled in the pertinent arts. For example, while it is a particular advantage of the preferred embodiment that it employs a conventional syringe, it may be modified for use with any number of specialized syringes that either are now available or that may be devised in the future. Also, the specific structure of the actuation element 44 described herein is exemplary only, and many alternative structures and configurations (such as, for example, a unitary structure instead of the multipart structure) may suggest themselves. Such modifications, as well as others that may suggest themselves, are considered to be within the spirit and scope of the present invention, as defined in the claims that follow.

What is claimed is:

1. Apparatus for delivering a liquid to a surgical site, comprising:
    a syringe having a barrel and a plunger that is axially movable within the barrel between a withdrawn (proximal) position and an inserted (distal) position, the plunger having a proximal end; and
    a syringe actuation device, comprising:
        a hollow, internally-threaded sleeve configured to receive the plunger in its withdrawn position, the sleeve having an open proximal end and a distal end opening configured for securing the syringe barrel; and
        a substantially cylindrical actuation element having an externally-threaded distal portion dimensioned to screw into the proximal end of the sleeve, and a plunger seat positioned in the distal portion of the actuation element to bear against the plunger so as to push the plunger axially toward its inserted position in the barrel as the actuation element is threaded into the sleeve.

2. The apparatus of claim 1, wherein the sleeve has a distal end slot dimensioned to receive the syringe barrel, and a longitudinal opening extending from the distal end slot toward the proximal end and dimensioned to receive the syringe plunger in its withdrawn position.

3. The apparatus of claim 2, wherein the distal end slot of the sleeve is in a distal end wall, and wherein the sleeve further comprises:
    a syringe barrel securing member extending distally from the distal end wall and communicating with the distal end slot, the securing member having an inside diameter dimensioned to receive the syringe barrel.

4. The apparatus of claim 3, further comprising:
    a removable insert configured to fit within the barrel securing member to reduce the inside diameter of the barrel securing member to accommodate a smaller syringe barrel.

5. The apparatus of claim 1, wherein the actuation element has a proximal portion configured as an enlarged-diameter hand grip.

6. The apparatus of claim 1, wherein the actuation element has a longitudinal axis and includes a recess in its distal end, and wherein the plunger seat comprises a surface in the recess that is transverse to the axis of the actuation element.

7. The apparatus of claim 6, wherein the plunger has a proximal end configured as a flattened thumb rest, and wherein the recess is configured to receive the thumb rest.

8. A device for actuating a syringe, wherein the syringe includes a barrel and a plunger movable axially within the barrel from a withdrawn (proximal) position to an inserted (distal) position, the device comprising:
    a hollow, internally-threaded sleeve configured to receive the plunger in its withdrawn position, the sleeve having an open proximal end and a distal end opening configured for securing the syringe barrel; and
    a substantially cylindrical actuation element having an externally-threaded distal portion dimensioned to screw into the proximal end of the sleeve, and a plunger seat positioned in the distal portion of the actuation element to bear against the plunger so as to push the plunger axially toward its inserted position in the barrel as the actuation element is threaded into the sleeve.

9. The device of claim 8, wherein the sleeve has a distal end slot dimensioned to receive the syringe barrel, and a longitudinal opening extending from the distal end slot toward the proximal end and dimensioned to receive the syringe plunger in its withdrawn position.

10. The device of claim 9, wherein the distal end slot of the sleeve is in a distal end wall, and wherein the sleeve further comprises:
    a syringe barrel securing member extending distally from the distal end wall and communicating with the distal end slot, the securing member having an inside diameter dimensioned to receive the syringe barrel.

11. The device of claim 10, further comprising:
    a removable insert configured to fit within the barrel securing member to reduce the inside diameter of the barrel securing member to accommodate a smaller syringe barrel.

12. The device of claim 8, wherein the actuation element has a proximal portion configured as an enlarged-diameter hand grip.

13. The device of claim 8, wherein the actuation element has a longitudinal axis and includes a recess in its distal and, and wherein the plunger seat comprises a surface in the recess that is transverse to the axis of the actuation element.

14. The device of claim 13, wherein the plunger has a proximal end configured as a flattened thumb rest, and wherein the recess is configured to receive the thumb rest.

15. A device for actuating a syringe, wherein the syringe includes a barrel and a plunger movable axially within the barrel from a withdrawn (proximal) position to an inserted (distal) position, the device comprising:
    a hollow, internally-threaded sleeve having an open proximal end, a distal end slot configured to receive the syringe barrel therethrough, and a longitudinal opening extending from the distal end slot toward the proximal end and dimensioned to receive the plunger in its withdrawn position; and
    a substantially cylindrical actuation element having a longitudinal axis, an externally-threaded distal portion dimensioned to screw into the proximal end of the sleeve, and a plunger seat positioned in the distal portion of the actuation element and comprising a surface transverse to the longitudinal access and configured to bear against the plunger so as to push the plunger axially toward its inserted position in the barrel as the actuation element is threaded into the sleeve.

16. The device of claim 15, wherein the distal end slot of the sleeve is in a distal end wall, and wherein the sleeve further comprises:
    a syringe barrel securing member extending distally from the distal end wall and communicating with the distal end slot, the securing member having an inside diameter dimensioned to receive the syringe barrel.

17. The device of claim 16, further comprising:
    a removable insert configured to fit within the barrel securing member to reduce the inside diameter of the barrel securing member to accommodate a smaller syringe barrel.

18. The device of claim 15, wherein the actuation element has a proximal portion configured as an enlarged-diameter hand grip.

19. The device of claim 18, wherein the plunger has a proximal end configured as a flattened thumb rest, and wherein the plunger seat is defined within a recess configured to receive the thumb rest.

* * * * *